(12) United States Patent
Morton

(10) Patent No.: US 9,889,097 B2
(45) Date of Patent: Feb. 13, 2018

(54) POWDER AND ITS METHOD OF MANUFACTURE

(75) Inventor: David Morton, Dorset (GB)

(73) Assignee: NANO4M LIMITED (GB)

( * ) Notice: Subject to any disclaimer, the term of this patent is extended or adjusted under 35 U.S.C. 154(b) by 858 days.

(21) Appl. No.: 12/666,498

(22) PCT Filed: Jun. 19, 2008

(86) PCT No.: PCT/GB2008/002152
§ 371 (c)(1),
(2), (4) Date: Jun. 21, 2010

(87) PCT Pub. No.: WO2009/001064
PCT Pub. Date: Dec. 31, 2008

(65) Prior Publication Data
US 2010/0266703 A1    Oct. 21, 2010

(30) Foreign Application Priority Data

Jun. 26, 2007    (GB) .................................. 0712316.9

(51) Int. Cl.
*A61K 9/14*    (2006.01)
*A61K 9/16*    (2006.01)
(Continued)

(52) U.S. Cl.
CPC ............ *A61K 9/5015* (2013.01); *A61K 9/145* (2013.01); *A61K 9/1676* (2013.01);
(Continued)

(58) Field of Classification Search
None
See application file for complete search history.

(56) References Cited

U.S. PATENT DOCUMENTS 4,079,441 A      3/1978   Bush et al.
4,609,675 A  *   9/1986   Franz ............................ 514/568
(Continued)

FOREIGN PATENT DOCUMENTS

GB       1511852 A      5/1978
GB       2125426 A      3/1984
(Continued)

OTHER PUBLICATIONS

Valverde Millán, José Manuel. "Introduction. The Classical Geldart's Diagram and the New Type of Gas-Fluidization Behavior." Fluidization of Fine Powders (2013): 1-6.*
(Continued)

*Primary Examiner* — Nissa Westerberg
(74) *Attorney, Agent, or Firm* — Fishman Stewart PLLC

(57) ABSTRACT

The invention relates to a novel powder, it's method of manufacture and the use thereof in powder material processing, particularly in the manufacture of components formed from compacted powder e.g. discs, monoliths, layers or tablets. The powders comprise coated host particles wherein over 70% of the mass of the powder comprises coated particles smaller than 100 microns. The powders have particular application in the pharmaceutical industry and the technology described can be used to control the properties of active pharmaceutical ingredients. The powders (10) may comprise drug particles (12), carrier particles (14) and additives (16).

20 Claims, 4 Drawing Sheets
(4 of 4 Drawing Sheet(s) Filed in Color)

(51) Int. Cl.
  *A61K 9/50*  (2006.01)
  *A61K 9/20*  (2006.01)
(52) U.S. Cl.
  CPC .......... *A61K 9/2077* (2013.01); *A61K 9/2081*
                  (2013.01); *A61K 9/2018* (2013.01)

(56) References Cited

U.S. PATENT DOCUMENTS

| | | | |
|---|---|---|---|
| 6,248,363 B1 * | 6/2001 | Patel .................... | A61K 9/1617 424/422 |
| 6,984,404 B1 * | 1/2006 | Talton et al. ................. | 424/490 |
| 2003/0133880 A1 | 7/2003 | Musa et al. | |
| 2005/0163843 A1 | 7/2005 | Boehm et al. | |
| 2005/0191357 A1 * | 9/2005 | Kawashima et al. ......... | 424/489 |
| 2005/0220996 A1 * | 10/2005 | Berger et al. ................. | 427/213 |
| 2005/0247608 A1 | 11/2005 | Collias et al. | |
| 2006/0127484 A1 * | 6/2006 | Speirs et al. .................. | 424/489 |
| 2007/0098804 A1 * | 5/2007 | Aronhime ................ | A61K 9/14 424/489 |

FOREIGN PATENT DOCUMENTS

| | | |
|---|---|---|
| JP | 60118676 A | 6/1985 |
| WO | WO-94/24994 A1 | 11/1994 |
| WO | WO-95/26715 A2 | 10/1995 |
| WO | WO-03/97013 A1 | 11/2003 |
| WO | WO 2005/104712 A1 * | 11/2005 |
| WO | WO 2006059152 A2 * | 6/2006 .............. A61K 9/008 |
| WO | WO-2006/069614 A2 | 7/2006 |
| WO | WO 2007057714 A2 * | 5/2007 ........... A61K 9/0043 |

OTHER PUBLICATIONS

English abstract provided for JP-2006241549.
English abstract for JP-2005336592.
International Search Report GB0703686.6, dated Jun. 1, 2007.
Bowen, P.: "Particle Size Distribution Measurement from Millimeters to Nanometers and from Rods to Platelets", Journal of Dispersion Science and Technology, Taylor and Francis Group, New York, NY vol. 23, No. 5, Jan. 1, 2002, pp. 631-662.
EP Office Action for Application No. 08762464.9, dated Jun. 30, 2014, 3 pp.
Zhou, Qi et al.: "Effect of mechanical dry particle coating on the improvement of powder flowability for lactose monohydrate: a model cohesive pharmaceutical powder", Journal of Powder Technology, 2011, pp. 414-421, doi: 10.2016/j.powtech.2010.11.028.

* cited by examiner

POWDER AND ITS METHOD OF MANUFACTURE

This application is a U.S. national phase of International application PCT/GB2008/002152 filed Jun. 19, 2008, which claims priority to Great Britain application DE 0712316.9, filed Jun. 26, 2007, which are hereby incorporated by reference in their entirety.

TECHNICAL FIELD

The present invention relates to a novel powder, it's method of manufacture and the use thereof in powder material processing, particularly in the manufacture of components formed from compacted powder e.g. discs, monoliths, layers or tablets.

BACKGROUND OF THE INVENTION

Compression, compaction, densification or sintering of powders are very common steps in powder material processing.

Powder material processing is important in, for example, the formation of structural ceramic components, electronic ceramic components (such as transducers, sensors, and batteries), metallic components (such as cermets and fuel cell electrodes), plastics, tabletted consumer goods (such as washing powders, nutraceuticals, and cosmetics), foods, agricultural products, veterinary products, crop products and pharmaceuticals (tablets).

In each of the above, compactability, compression, segregation and flow are key factors, and such factors depend on the surface property and shape of the particles in the powder.

Compacts such as material discs or tablets often comprise a number of additives in addition to one or more functional ingredients (hereafter host) which may be active ingredients or excipients. This is notably the case in tablets. The main additives include, but are not limited to: diluents or fillers; binders (which may be used to bind the powders together); disintegrants (which help the compacts to break up and dissolve); glidants (which are used to improve granule flow); anti-adherent or lubricants (which help the release of the compressed compact from the die); and anti-adhesives (which are sometimes used to prevent film residue being left on the die/punch). In addition, colourings, flavourings, sweeteners, buffers and adsorbents may be used.

Compacts are typically made by compressing a powder of particulate solid between two punches in a die of a compact press. For the ingredients to be transformed into compacts of satisfactory quality, the formulation must have the key attributes of suitable flow, fluidity and compressibility.

More specifically the powders used should have the following attributes:

Firstly, the formulation must flow into the die space of the press sufficiently rapidly and in a reproducible manner. Otherwise, unacceptable variation in compact weight, homogeneity in structure and content will ensue;

Secondly, the particles in the formulation must cohere when subject to a compressing force, and that coherence should remain after the compressive force has been removed; and Thirdly, after the compression event is complete, it must be possible for the compact to be removed from the press without damage to either the compact or the press.

Very few functional or active ingredients possess all three of these attributes in their original state, and indeed many possess none. Thus they require processing and subjection to treatments with other additive materials in order that the desired characteristics can be achieved.

Prior art identified, primarily in the ceramics field, include:

WO 2006/069614 which discloses a composite powder material comprising a hard particulate phase coated by cobalt or nickel;

JP 2006-241549 which discloses a metal tin fine powder having a fine particle diameter;

JP 2006 147959 which discloses magnetic powders containing small diameter soft magnetic metal powders of 10-80% by weight coated by an insulating material and bonding agent which are then press molded and hardened;

JP 60 118676 which discloses a hot pressing mixtures of ceramic powders and organic thermoplastic material;

KR 2005 0076148 which discloses copper coated amorphous powders of various metals; and U.S. Pat. No. 4,079,441 which discloses tantalum powders with a particle core size from 30 µm to 2.5 µm.

All this prior art relates to the field of ceramics.

An object of this invention is to provide powders which have characteristics making them more suitable for compaction, a method of manufacturing such powders which is both simple and cost effective and compacts such as tablets which may be obtained from the powders of the invention.

In particular, it is concerned with pharmaceutical applications, particularly, though not exclusively, oral delivery, other solid dose forms which may be injected or implanted, as well as trans-dermal products such as patches and creams.

SUMMARY OF THE INVENTION

By ensuring the surface of the powder particles are effectively covered by an ultra-thin layer of an appropriate additive, and optionally are also mechanically smoothed and/or rounded in the process, it has been determined that the powder particles have a reduced level of adhesion, cohesion and friction and thus the powders lend themselves well to compaction.

The powders of the invention exhibit improved flow, increased bulk and tap density compared to powder particles of an equivalent diameter which have not been coated.

Furthermore, the powders of the invention may, as a consequence, be more rapidly, effectively or efficiently sintered into a resulting body, and the final quality of the sintered body may be improved, for example in terms of strength, electrical conductivity or other properties well know in the art.

The bioavailability of a drug may also be altered and the size may make such powders particular useful when present in e.g. creams or patches for trans-dermal delivery.

According to a first aspect of the present invention there is provided a powder, for use in the manufacture of a product for delivery to a human or animal, characterized in that it comprises coated host particles and wherein over 70% of the mass of the powder comprises coated particles smaller than 100 microns.

Preferably over 80% more preferably still over 90%, through 92%, 94%, 96% to greater than 98% of the mass of the powder comprises coated particles smaller than 100 microns.

Alternatively the percentage distribution of coated particles smaller than 100 microns may be greater than 80% more preferably still over 90%, through 92%, 94%, 96% to greater than 98% by number.

According to a second aspect of the present invention there is provided a method of manufacturing a powder of the invention comprising mixing a host material with a coating material under conditions which generate high shear and compressive forces sufficient to cause the coating material to coat the host material.

A sufficient force is, for example, one obtained by a rotating blade in a vessel at speeds greater than 2000 rpm.

According to a third aspect of the present invention there is provided a product for delivery to a human or animal manufactured from a powder of the invention.

The product or compact may be a tablet, or other solid dosage form such as an implant.

This novel approach to compacting set out below allows relatively low levels, for example, less than 10%, more preferably less than 5%, through 3%, 2%, 1%, and most preferably less than 0.5% of one or more additives, such as, for example, an anti-adherent or a lubricant to be efficiently used compared to previously known methods.

Additionally, and in contrast to the known problems experienced in tablet formation, the coatings on the small host particles do not lead to compact weakness, as experienced in the art. This is because the nature of the coating and the surface are novel, compared to existing methods for adding lubricants. For example, very thin coatings may be produced, surface deformation may occur and lubricant layers may be deformed into the surface.

Also, where the coating comprises a lubricant it has been found that compact release from the die is very effective.

The coated particles making up the powders of the invention have an unusually small mean particle size (less than 100 microns) for powders provided for compacting and furthermore the powders have a very high proportion of particles of this size—typically greater than 80% by mass.

These powders, comprising coated particles which are smaller than the particles conventionally present in compacts, at least when present to such a high degree by mass, are suitable for compacting as a consequence of their improved flow which is a result of their coating and surface treatment. They also compress more easily, and form stronger compacts. Additionally they may sinter more effectively on further processing/heating.

This is believed to be because the smaller particles have a much higher surface area and surface energy, and are thus more easily compressed into strong compacts, than known compositions.

Further, using known powders, the flow of such small sized powders is usually very poor, as these are too cohesive to fill the compact dye with sufficient consistency.

The powders comprising the coated particles of the invention have been found to have significantly improved flow characteristics.

Preferably the coated particles lie within the size range of from 0.001 µm to 200 µm, more preferably from 0.1 µm to 100 µm, more preferably still from 0.1 µm to 80 µm, through 0.1 µm to 60 µm, to 0.1 µm to 40 µm, and most preferably from 0.1 µm to 20 µm as this provides for improved compression.

Preferably the coated particles have a mass median diameter of less than 200 µm, more preferably less than 100 µm, more preferably still less than 60 µm, more preferably still less than 40 µm, more preferably still less than 30 µm, most preferably less than 20 µm, to less than 15 µm, most preferably less than 10 µm, as this provides for improved compression.

Preferably, where the coated particles are drug particles or comprise drug containing particles, these coated particles have a mass median diameter of greater than 5 µm, more preferably greater than 7 µm, more preferably still greater than 8 µm, more preferably still greater than 10 µm, more preferably still greater than 15 µm, and most preferably greater than 20 µm.

Because of the high degree of thin layer coating, and the similar size of the coated particles in the mix, regardless of composition, it is possible for all coated particles to appear substantially the same. Consequently, any composition mixture of different host particles is possible, allowing much greater flexibility of composition to be formed.

In the context of particles, the term "size" is understood to refer to the geometric diameter or geometric equivalent diameter of the particle, typically as measured by laser diffraction, by time of flight sizer or by microscopy.

Generally in any powder manufacturing process, powder must flow, from a hopper into the feed frame of a compact machine. The powder may flow under gravity, optionally with some agitation, but resisting segregation. The powders should resist faults such as "bridging", "badger splitting" or "rat-holing". The powders of the present invention additionally overcome these problems as the coating provides for improved fluidity.

Additionally, the flow must ensure that the die cavity is filled consistently, completely and uniformly. Advantageously, the invention allows small near spherical particles to be used, although other shapes may also be used in the invention, such as plates, needles, angular or other irregular forms. Spheres are preferred as these offer minimum interaction with walls of the compact machine and provide flow uniformly. The method of the invention may improve the shape, such as increase the sphericity of the particles, by the distortion of the original particle shapes. In the absence of this desired flow, granulation may be required. This adds significant extra complexity and cost to the process.

Preferably the particles of the invention are coated to reduce the tribo-electric charging of the powder such that the materials have a minimum electrostatic charge.

Some spread in particle size may be advantageous to provide a size distribution with good packing efficiency. Bi or multi-modal size distributions may be advantageously used, which are known to provide more efficient packing.

In addition, the powder density of the coated particles is higher than uncoated particles of comparable materials with the same size distribution. This may be bulk aerated density or tapped density, as measured according to the United States Pharmacopeia. Preferably the measurement is bulk aerated density. For example, coated materials of the invention may be at least 25% denser, through 40% denser, 70% denser, and 100% denser, and 125% denser to as much as 150% denser or more after the processing of uncoated materials.

The powder density of the coated particles can be at least 25% more than that of an equivalent unprocessed host material with the same size distribution.

In addition, the powder Hausner ratio of the coated particles is lower than uncoated particles of comparable materials with the same size distribution. This may be determined from the bulk aerated density and bulk tapped density, as measured according to methods outlined by the United States Pharmacopeia. For example, coated materials of the invention may have Hausner ratios reduced by 5%, through 10%, and 20%, to as much as 50% as compared to uncoated materials. The absolute values of the Hausner ratios of the treated powders may be less than 1.5, 1.4, 1.35, 1.3 or even 1.25.

Hausner ratio is a well established measure of powder flow. The invention leads to the improvement in powder flow properties, and this improvement may be measured in a number of ways, known to those skilled in the art. These include, but not limited to, the Carrs index (for example, the absolute values of the Carrs Index of the treated powders may be less than 0.40, 0.35, 0.30, 0.28 or even 0.25), Angle of repose (for example, the absolute values of the angle of repose of the treated powders may be less than 50, 40, 35, 30 or even 27 degrees), FlowRatex, ring shear testing, and Freeman FT4 powder rheometer.

This invention allows use of similar small size particles of multi-component compositions without segregation. Segregation occurs in most systems due to particle size differentiation. Segregation is reduced because all particles are approximately in the same or sufficiently similar or overlapping particle size distributions.

This invention also improves lubrication of all particles and protects heat sensitive particles by reducing heat build-up due to friction on compression.

The invention additionally allows each particle to be coated to provide specific properties, including rapid dissolution, rapid wetting, rapid disintegration, delayed dissolution, and timed release by selection of the coating material.

The coating process allows one to reduce the influence of plastic/elastic deformation properties of the host materials, and consequently allows the facile compaction of otherwise difficult to compact materials.

The coating process also increases the stability of composite components by reducing any interactions or unwanted chemical or physical reaction with other components at any stage of manufacture or storage. Further, the coating may reduce the interaction components with moisture or any gases (such as oxidation) or light or any other external influence.

The powders of the invention may also be used to form composite compacts such as multilayered compacts.

The final compact formed from the powders of the invention may benefit from one or more of the following:
  Strength to withstand the rigors experienced during further production, packaging transport and dispensing;
  Consistency in form and elimination of faults, cracks, chips, contamination, capping etc. . . . . .
  Excellent chemical and physical stability, during normal or harsh storage conditions.

The resulting compact, tablet or powder may be subsequently heated to remove the surface lubricant, or any other volatile or decomposable constituent. This may or may not leave voids in the structure which may have some functional benefit, such as controlled porosity.

In a preferred embodiment, powder materials are coated by an additive lubricant-type material. The lubricant can comprise any known compact lubricant. In preferred embodiments, the lubricant is any one or a mixture selected from the following: a metal stearate such as magnesium stearate, calcium stearate, Zinc stearate, or sodium stearate. Other preferred materials include salts, esters and other derivatives of stearates, palmitates, behenates and other fatty acids, from carbon chain length C6 to C35, which includes saturated as well as unsaturated chains, cis and trans isomers. Further preferred materials include PRUV® (sodium stearyl fumarate), COMPRITROL® (glyceryl behenate), sodium stearyl lactylate, sodium lauryl sulphate, and amino acids such as leucine. All known lipids and phospholipids are included, such as lecithin, DPPC, DPPE, DPPI. Inorganic lubricants, such as colloidal silica (such as a CABO-SIL grade or an AEROSIL grade), colloidal alumina, colloidal titania and talc are also included as additives, plus any alternative known inorganic particles in the sub-micron size range from 1 nm to 1 μm such as titania, alumina, iron oxide, zinc oxide, including any fumed metal oxide nanoparticles. In such nanoparticle it is proposed that the nanoparticles can lubricate constituent fine powders to provide flow yet when under compression may be pressed below the surface of the coated particles, removing them from the surface contact barrier role, again yielding sufficient particle-particle contacts to form strong tablets. In addition, these inorganic nanoparticles may be surface treated to be made hydrophobic or hydrophilic, or surface modified with polymeric additives. For the avoidance of doubt, this list of lubricants may also include any polymorph, and hydrate of these materials and any source of material, including synthetic, vegetable, mineral or animal.

It may be advantageous for the additive to be water soluble or wettable, such that dissolution of the resulting material is not retarded by the additive. Alternatively it may be advantageous for the additive to be hydrophobic, such that dissolution of the resulting material is retarded by the additive.

Particle coating may permit use of excipients or drugs that are otherwise difficult to formulate. For example, Mannitol has become a popular excipient for chewable tablets as it gives a cool taste sensation on dissolving due to its negative heat of salvation. The excipient is also used in conventional tablets because it does not absorb water and can protect water sensitive molecules from degradation. However, mannitol's crystal structure favours the creation of large particles which has made it difficult to produce a version with the desired particle size, control and flow-ability. By suitable size reduction and coating, mannitol can be used as a suitable excipient which had previously been problematic, and does not require complex mixing and granulation steps. This could equally apply to a drug that was problematic in this manner.

In a further embodiment, powders are produced with improved flow for filling into capsules, as an alternative form of oral drug delivery to compression into tablets. Powders may comprise any of the components already mentioned.

In a further embodiment, powders may be coated to achieve a controlled release to avoid problems of drug abuse in a tablet or capsule or other form. If chewed, crushed or dissolved in water, tablets of many conventional controlled release formulations can expose the entire dose of drug, which can leads to a drug high, the potential for future drug abuse, and possible death. Due to the small size of particles, where each one is coated to achieve the sustained release, this sustained-release oral dosage form is inherently designed to be more resistant to tampering and abuse than traditional formulations of the drug. This could help in the case of some elderly patients, who are known to crush tablets to make them easier to swallow: In this case, controlled release coatings (or similarly enteric coatings) would be less likely to be disrupted significantly.

Coating of drug particles may also achieve taste masking. This is essentially achieved by encapsulating each particle of the drug substance in a continuous membrane which forms an inert barrier between the drug and the taste buds. By coating each particle with suitable membranes with varying degrees of thickness and porosity, various effects may be achieved. The membranes used can be modified for each product according to specific requirements such as gastrointestinal release rate or final dosage form. This may include orally disintegrating tablets, chewable tablets or sprinkles and may also be used to convert liquid formulations to solid ones. Such features may provide a better taste and feel and can consequently improve patient compliance, where poor-tasting or awkward dosage forms can reduce the chances that patients stick to a course of medication.

In addition, by suitable coating of drug and excipients with a suitable additive, wetting of particles can be enhanced, which facilitates rapid water adsorption and oral disintegration resulting in tablets with a reduced disintegration time for example, of less than 1 minute, or less than 30 seconds, or even less than 15 seconds. Such fast melt formulations are achieved with high drug loads possible, such as greater than 50%, greater than 60% or even greater than 80%, in this simple dry blending step, for use in tablets, capsules or powder sprinkles.

In some embodiments, drug powders may have specific handling problems, for example it may be produced with very fine particle size, in fine needle shapes or have low density, or have a rough surface: all of which as examples, but not limited to, can cause adhesion and flow problems. The invention can resolve such problems by providing coatings and by modifying the particle shape, and by partial agglomeration of particles, which effects can improve the flow, and reduce adhesion.

Some powders may have susceptibility to significant electrostatic charging which causes handling problems. By suitable coating, the electrostatic charging is reduced.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
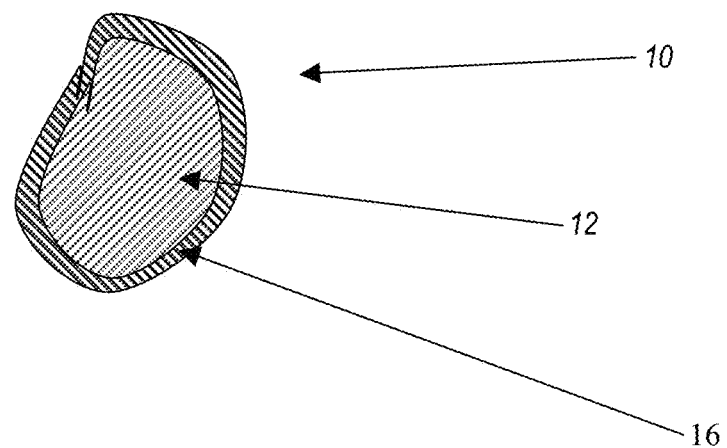
FIG. 1 is a diagram illustrating the coating of an additive lubricant layer on a drug host particle.

Referring to FIG. 1, it is possible to form powders (10) of the invention by, for example, coating small drug particles (12), sized in the ranges noted above, with an additive comprising for example a smeared waxy film or nanoparticles (16), which results in improved flow. Additional additive materials may be built up thereon or co-added, and optionally layers of other additives, such as controlled release layers or taste masking layers can be provided.

Figure 2:
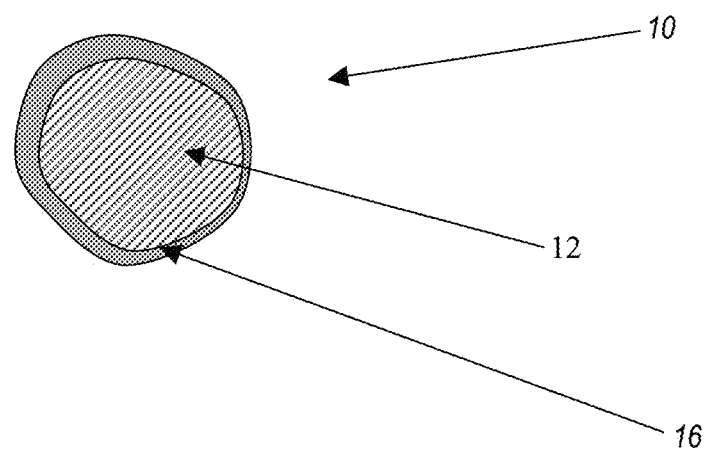
FIG. 2 is a diagram illustrating the coating of an additive lubricant layer on an excipient host particle.

Referring to FIG. 2, it is possible to form powders (10) of the invention by, for example, coating small drug particles (12), sized in the ranges noted above, with an additive comprising for example a smeared waxy film or nanoparticles (16), which results in improved flow.

Figure 3:
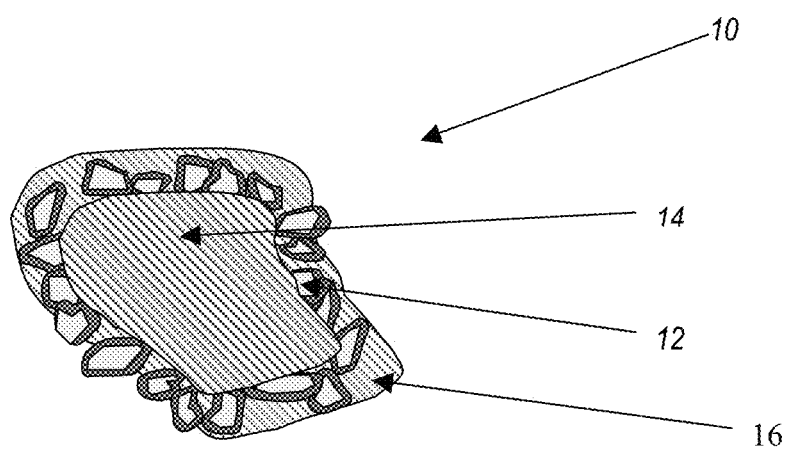
FIG. 3 is a diagram illustrating the embedding of small drug particles on a host particle and it's coating with an additive.

Referring to FIG. 3, it is possible to form powders (10) of the invention by, for example, embedding very small drug particles (12), for example less than 1 micron, onto carrier particles (14) sized in the ranges noted above, together with an additive (16), which results in improved flow. For instance, it is known than milling drug powders or precipitating materials to form sub-micron drug containing particles may increase drug dissolution of poorly soluble drugs, as anticipated by the Noyes Whitney equation. This is caused by their increased surface area. However, such materials often termed nanoparticles, are also prone to agglomeration due to their high surface energy. In such cases, if these particles are not stabilized in their finely divided form, the benefit of increased surface area is lost, and improved dissolution is not obtained. By embedding sub-micron drug particles onto host particles, together with an additive agglomeration can be prevented The host particles may be any suitable excipients or drug, which is most preferably, though not essentially, water soluble. The host particles are preferably small, such as less than 20 μm, more preferably less than 15 μm, more preferably still less than 10 μm and most preferably less than 5 μm.

Figure 4:
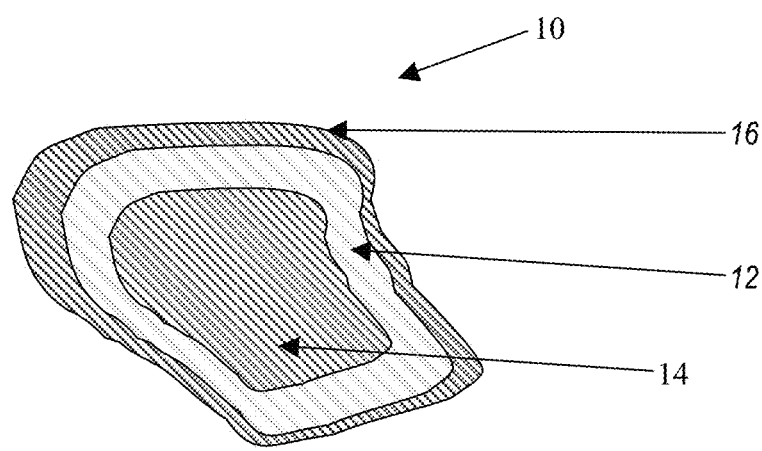
FIG. 4 is a diagram illustrating the smearing of a drug onto a host particle and it's coating with an additive.

The host particle provides a high surface area to be maintained for dissolution. These small particles flow well due to the factors described above. The additive is preferably easily wettable, or water soluble. The surprisingly good flow allows these powders to be tabletted or filled into capsules. The process for producing sub-micron drug particles may include any technique known to those skilled in the art such as, but not be limited to, ball milling, bead milling, homogenizing, or rapid precipitation, Referring to FIG. 4 there is illustrated an example where a powder of the invention (10) is formed by spreading a poorly soluble drug (12), or an extract such as a botanical drug substance, which is or comprises soft or waxy material and is not suitable for milling or producing sub-micron particles, in a sub-micron layer over a host particle (14). The soft poorly soluble drug may be co-milled together with one or several other additive materials to form a homogeneously mixed layer. This mixture may be designed to improve the solubility of the soft or waxy drug, such that the other additives improve the wetting or dissolution rate of the drug.

Again the host particles may be any suitable excipients or drug, preferably water soluble, and of a size such as less than 20 μm, less than 15 μm, less than 10 μm to less than 5 μm. Again, this provides a high surface area of the soft drug, to be maintained for improved dissolution. Additional e.g. additive materials (16) may be built up thereon. Alternatively, several drugs in multiple layers, and optionally layers of other additives, such as flow aids or taste masking layers can be provided.

The novel powders of the invention derive from the use of high energy processing methodology. Such high energy methods have not previously been used in the context of coating and preparing particles for compression.

In a preferred embodiment, the high energy method includes a mechano-chemical bonding technique as outlined by Pfeifer et al (Powder Technology 117, p 40, 2001). All methods so described in the art are suitable, and include but are not limited to, NARA™ HYBRIDISER or Ball or Bead mill, and HOSOKAWA™ CYCLOMIX, MECHANOFUSION, NOBILTA, NANOCULAR or FACULTY processing/mixing systems. The process may involve a rotor in a vessel, wherein the rotor has a very high tip speed, preferably greater than 5 m/s, more preferably greater than 10 m/s through 15 m/s, 20 m/s, 25 m/s, 30 m/s, 35 m/s, 40 m/s and 45 m/s to greater than 50 m/s. The process may be a dry process or be conducted in the presence of a fluid/liquid.

The method may include any other form of milling, such as jet milling, pin milling, or end runner milling.

The method of the invention generally involves bringing the particles of one or more additives into close contact with the surfaces of the one or more host particles. In order to achieve coated particles, a degree of intensive mixing is required to ensure a sufficient break-up of agglomerates of constituents, dispersal and even distribution of additive(s) over the host active particles.

A substantial degree of mixing may be required to ensure a sufficient break-up of agglomerates of constituents, dispersal and even distribution of additive particles over the host particles. For example, simple contact adhesion may be insufficient and a stronger embedding or fusion of particles of additive material onto host particles is required to enhance the structure and functionality of the coating.

Where there are advantages to distorting and/or embedding the particles of additive material substantially onto the host particle, a substantial degree of energy is required from the milling. In this case, the particles of additive material may experience sufficient force to soften and/or break, to distort and to flatten them. These processes are enhanced by the presence of the relatively harder host particles which act as a milling media as well as a de-agglomerating media for such processes. As a consequence of this process the particles of additive material may become wrapped around the core active particle to form a coating. These processes are also enhanced by the application of a compression force.

As a consequence of the milling step, complete or partial, continuous or discontinuous, porous or non-porous coatings may be formed. The coatings originate from a combination of host particles and particles of additive material. They are not coatings such as those formed by wet processes that require dissolution of one or both components. In general, such wet coating processes are likely to be more costly and more time consuming than the milling process and also suffer from the disadvantage that it is less easy to control the location and structure of the coating.

The coatings may comprise mixes of more than one additive, for example a mix of more than one waxy soft additive to form an intimate mix with different properties, or a mix of more than one type of nanoparticle additive to form an intimate mix with different properties, or combinations of soft waxy additives and nanoparticle additives.

Preferably, the milling step involves the compression of the mixture of active particles and particles of additive material in a gap (or nip) of fixed, predetermined width (for example, as in the HOSOKAWA™ MECHANO-FUSION, NOBILTA, NANOCULAR and CYCLOMIX methods).

Some preferred milling methods are described below in greater detail.

MECHANO-FUSION:

As the name suggests, this dry coating process is designed to mechanically fuse a coating material onto a host material.

The coating material is generally smaller and/or softer than the host material. The MECHANO-FUSION and related process working principles are distinct from alternative milling techniques in having a particular interaction between inner element and vessel wall, and are based on providing energy by a controlled and substantial compressive force, with high speed rotation.

The fine host particles and the additive particles are fed into the MECHANO-FUSION driven vessel, where they are subject to a centrifugal force and are pressed against the vessel inner wall. The powder is compressed between the fixed clearance of the drum wall and a curved inner element with high relative speed between drum and element. The inner wall and the curved element together form a gap or nip in which the particles are pressed together. As a result the particles experience very high shear forces and very strong compressive stresses as they are trapped between the inner drum wall and the inner element (which has a greater curvature than the inner drum wall).

The particles violently collide against each other with enough energy to locally heat and soften, break, distort, flatten and wrap the particles of additive material around the core host particle to form a coating. The energy is generally sufficient to break up agglomerates and some degree of size reduction of both components may occur. Embedding and fusion of particles of additive material onto the active host particles may occur, facilitated by the relative differences in hardness (and optionally size) of the two components.

Either the outer vessel or the inner element may rotate to provide the relative movement. The gap between these surfaces is relatively small, and is typically less than 10 mm and is preferably less than 5 mm, more preferably less than 3 mm. This gap is fixed, and consequently leads to a better control of the compressive energy than is provided in some other forms of mill such as ball and media mills. Also, preferably, no impaction of milling media surfaces is present so that wear and consequently contamination are minimised.

The speed of rotation may be in the range from 200 to 40,000 rpm, preferably 2,000 to 20,000 rpm. A scraper may also be present to break up any caked material building up on the vessel surface. This is particularly advantageous when using fine cohesive starting materials. The local temperature may be controlled by use of a heating/cooling jacked built into the drum vessel walls.

The powder may be re-circulated through the vessel.

CYCLOMIX Method (Hosokawa Micron):

The CYCLOMIX comprises a stationary conical vessel with a fast rotating shaft with paddles which move close to the wall. Due to the high rotational speed of the paddles, the powder is propelled towards the wall, and as a result the mixture experiences very high shear forces and compressive stresses between wall and paddle. Such effects are similar to the MECHANO-FUSION as described above and may be sufficient to locally heat and soften, to break, distort, flatten and wrap the particles of coating material, e.g. a hydrophobic material, around the active particles to form a coating. The energy is sufficient to break up agglomerates and some degree of size reduction of both components may also occur depending on the conditions and upon the size and nature of the particles.

HYBRIDISER Method:

This is a dry process which can be described as a product embedding or filming of one powder onto another. The fine active particles and fine or ultra fine particles of e.g. hydrophobic material are fed into a conventional high shear mixer pre-mix system to form an ordered mixture. This powder is then fed into the HYBRIDISER. The powder is subjected to ultra-high speed impact, compression and shear as it is impacted by blades on a high speed rotor inside a stator vessel, and is re-circulated within the vessel. The active host particles and particles of e.g. a hydrophobic coating material collide with each other. Typical speeds of rotation are in the range of 5,000 to 20,000 rpm. The relatively soft fine additive particles experience sufficient impact force to soften, break, distort, flatten and wrap around the active particle to form a coating. There may also be some degree of embedding into the surface of the active particles.

Other preferred methods include ball and high energy media mills which are also capable of providing the desired high shear force and compressive stresses between surfaces, although as the clearance gap is not controlled, the coating process may be less well controlled than for MECHANO- FUSION milling and some problems such as a degree of undesired re-agglomeration may occur. These media mills may be rotational, vibrational, agitational, centrifugal or planetary in nature.

Pestle and mortar mills are other mills which also provide a very high shear force and compressive stresses between surfaces.

The size of the particles of additive material after the milling step is preferably significantly less than the size of the host particles, to enable the additive materials to more effectively coat the surfaces of the host particles. As noted above, the particles of additive material preferably become smeared over or fused to the surfaces of the particles of host material, thereby forming a coating which may be substantially continuous or discontinuous. Where the coating is discontinuous, it Preferably covers on average of at least 50% (that is, at least 50% of the total surface area of the active particles will be covered by additive material), more advantageously at least 70% and most preferably at least 90% of the surfaces of the host particles.

The coating is preferably on average less than 1 μm, more preferably less than 0.5 μm, more preferably less than 0.2 μm, more preferably less than 0.1 μm, more preferably less than 50 nm, more preferably less than 20 nm and most preferably less than 10 nm thick.

The milling may be wet milling, that is, the milling step may be carried out in the presence of a liquid. That liquid medium may be high or low volatility and of any solid content as long as it does not dissolve the particles to any significant degree and its viscosity is not so high that it prevents effective milling. The liquid medium preferably is not aqueous.

It has been found that the MECHANO-FUSION and CYCLOMIX techniques referred to above often provide the microparticles as individual, that is, unagglomerated microparticles. That is in contrast to less controlled methods such as ball milling, which have been found to often produce the microparticles in the form of agglomerated microparticles.

The properties of some pharmaceutical drugs or materials processed using methodology as described above are set out below:

Example 1

Drug A with a mass median particle size of 10 microns and magnesium stearate were combined in the ratio 50:1 by weight. The blend was then processed in a MECHANO-FUSION AMS-Mini (Hosokawa) as follows: The sample was premixed for 5 minutes by running the machine at 1000 rpm. The machine speed was then increased to 5000 rpm for 30 minutes.

The poured and tapped density of this powder approximately doubled. This experiment was repeated for drug samples with mass median particle sizes of approximately 20 and 30 microns and similar results were obtained.

Example 2

Drug A with a mass median particle size of 20 microns and colloidal silica were combined in the ratio 20:1 by weight. The blend was then processed in a MECHANO-FUSION AMS-Mini (Hosokawa) as follows: The sample was premixed for 5 minutes by running the machine at 1000 rpm. The machine speed was then increased to 5000 rpm for 10 minutes.

The poured and tapped density of this powder approximately doubled. This experiment was repeated for drug samples with mass median particle sizes of approximately 20 and 30 microns and similar results were obtained.

Example 3

Lactose (SORBOLAC 400) with a mass median particle size of about 8 microns and magnesium stearate were combined in the ratio 50:1 by weight. The blend was then processed in a MECHANO-FUSION AMS-Mini (Hosokawa) as follows: The sample was premixed for 5 minutes by running the machine at 1000 rpm. The machine speed was then increased to 5000 rpm for 30 minutes.

The poured and tapped density of this powder approximately doubled. This experiment was repeated for lactose samples with a mass median particle size of approximately 20 microns, 30 microns, 40 microns and 60 microns and similar results were obtained.

Example 4

Drug A with a mass median particle size of 10 microns, lactose (SORBOLAC 400) with a mass median particle size of about 8 microns and magnesium stearate were combined in the ratio 20:20:1 by weight. The blend was then processed in a MECHANO-FUSION AMS-Mini (Hosokawa) as follows. The sample was premixed for 5 minutes by running the machine at 1000 rpm. The machine speed was then increased to 5000 rpm for 30 minutes.

The poured and tapped density of this powder approximately doubled. This experiment was repeated for drug samples with mass median particle sizes of approximately 20 and 30 microns and similar results were obtained.

Example 5

Drug A with a mass median particle size of 30 microns, lactose (PHARMATOSE 450) with a mass median particle size of about 20 microns and magnesium stearate were combined in the ratio 30:20:1 by weight. The blend was then processed in a MECHANO-FUSION AMS-Mini (Hosokawa) as follows. The sample was premixed for 5 minutes by running the machine at 1000 rpm. The machine speed was then increased to 5000 rpm for 30 minutes.

The poured and tapped density of this powder approximately doubled.

Example 6

Five commercially-available milled lactoses were studied: RESPITOSE MC001, LACTOHALE 300, SORBOLAC 400, PHARMATOSE 450M and PHARMATOSE 300M. The powders were coated with an estimated minimum (5%, 2%, 2%, 1%, 0.5% respectively) of magnesium stearate (Mallinckrodt Chemicals) or CABOSIL colloidal silica (Cabot), using a NOBILTA 130 (Hosokawa Micron Corporation). Bulk aerated and tap densities were measured manually in a measuring cylinder. The averaged aerated bulk density values, Tapped density values and calculated Carrs Index are provided in Table 1 below, for the five lactoses. Surprisingly, the SORBOLAC 400, with median size 8 um, increases in density by nearly 140% following co-processing with magnesium stearate.

The CABOSIL samples exhibited a lesser improvement; however the process conditions and quantities were not optimised for this additive.

TABLE 1

| | | | Poured density (g/ml) | Tapped density (g/ml) | Carr index |
|---|---|---|---|---|---|
| Respitose MC001 (2 um) | Untreated | Mean | 0.22 | 0.46 | 0.52 |
| | | SD | 0.01 | 0.01 | 0.03 |
| | Mechanofused/Mgst | Mean | 0.45 | 0.71 | 0.37 |
| | | SD | 0.02 | 0.01 | 0.01 |
| | | Increase (%) | 104.17 | 55.22 | −28.57 |
| Lactohale 300 (5 um) | Untreated | Mean | 0.22 | 0.48 | 0.54 |
| | | SD | 0.00 | 0.02 | 0.01 |
| | Mechanofused/Cabosil | Mean | 0.24 | 0.51 | 0.53 |
| | | SD | 0.01 | 0.03 | 0.01 |
| | | Increase (%) | 7.64 | 5.33 | −1.89 |
| | Mechanofused/Mgst | Mean | 0.48 | 0.73 | 0.33 |
| | | SD | 0.02 | 0.03 | 0.04 |
| | | Increase (%) | 118.95 | 51.99 | −37.88 |
| Sorbalac 400 (8 um) | Untreated | Mean | 0.28 | 0.61 | 0.54 |
| | | SD | 0.00 | 0.02 | 0.01 |
| | Mechanofused/Cabosil | Mean | 0.35 | 0.69 | 0.49 |
| | | SD | 0.01 | 0.01 | 0.01 |
| | | Increase (%) | 24.11 | 12.76 | −8.50 |
| | Mechanofused/Mgst | Mean | 0.67 | 0.92 | 0.27 |
| | | SD | 0.02 | 0.01 | 0.02 |
| | | Increase (%) | 139.59 | 51.21 | −49.80 |
| Pharmatose 450M (20 um) | Untreated | Mean | 0.38 | 0.76 | 0.50 |
| | | SD | 0.00 | 0.02 | 0.01 |
| | Mechanofused/Cabosil | Mean | 0.45 | 0.85 | 0.47 |
| | | SD | 0.01 | 0.01 | 0.01 |
| | | Increase (%) | 17.86 | 11.93 | −5.27 |
| | Mechanofused/Mgst | Mean | 0.72 | 1.04 | 0.31 |
| | | SD | 0.01 | 0.00 | 0.01 |
| | | Increase (%) | 90.26 | 37.43 | −38.38 |
| Pharmatose 350M (30 um) | Untreated | Mean | 0.44 | 0.80 | 0.46 |
| | | SD | 0.01 | 0.01 | 0.01 |
| | Mechanofused/Cabosil | Mean | 0.60 | 0.94 | 0.36 |
| | | SD | 0.00 | 0.02 | 0.02 |
| | | Increase (%) | 37.82 | 17.72 | −20.38 |
| | Mechanofused/Mgst | Mean | 0.69 | 0.99 | 0.30 |
| | | SD | 0.01 | 0.02 | 0.02 |
| | | Increase (%) | 59.56 | 23.75 | −34.47 |
| Pharmatose 200M (40 um) | Untreated | Mean | 0.52 | 0.95 | 0.45 |
| | | SD | 0.01 | 0.01 | 0.01 |
| | Mechanofused/Cabosil | Mean | 0.66 | 0.96 | 0.32 |
| | | SD | 0.01 | 0.01 | 0.01 |
| | | Increase (%) | 25.60 | 1.51 | −28.94 |
| | Mechanofused/Mgst | Mean | 0.71 | 0.95 | 0.26 |
| | | SD | 0.01 | 0.02 | 0.01 |
| | | Increase (%) | 35.62 | 0.14 | −43.26 |

Example 7

Drug A with a mass median particle size of 10 microns, lactose (SORBOLAC 400) with a mass median particle size of about 8 microns and magnesium stearate were combined in the ratio 10:10:1 by weight. The blend was then processed in a MECHANO-FUSION AMS-Mini (Hosokawa) as follows. The sample was premixed for 5 minutes by running the machine at 1000 rpm. The machine speed was then increased to 5000 rpm for 30 minutes.

The poured and tapped density of this powder approximately doubled. This experiment was repeated for drug samples with mass median particle sizes of approximately 20 and 30 microns and similar results were obtained.

Example 8

Ibuprofen with a mass median particle size of 40 microns, lactose (PHARMATOSE 350) with a mass median particle size of about 30 microns and magnesium stearate were combined in the ratio 30:30:1 by weight. The blend was then processed in a MECHANO-FUSION AMS-Mini (Hosokawa) as follows. The sample was premixed for 5 minutes by running the machine at 1000 rpm. The machine speed was then increased to 5000 rpm for 30 minutes.

Example 9

A model fine drug powder (salicylic acid), (VMD ~20 um) was placed in a Hosokawa Micron AMS Mini MECHANOFUSION system, and processed with 1% and 5% w/w magnesium stearate lubricant at ~6000 rpm for 10 minutes. This process was repeated with Extra Fine grade lactose (VMD ~15 um) and 0.5% and 5% w/w magnesium stearate. These powders were very free flowing after processing, and their density was substantially increased (approx doubled).

These coated powders were blended by tumbling for 5 minutes. Mixed and original powders were fed into a laboratory tablet press with a single 12 mm flat faced die and punch set. As a benchmark, a direct compression lactose was also fed into the press. Compaction pressure was increased to a maximum load where the press overloaded in each case. Tablets were produced at a load just below this point. Powder flow appeared suitable in the coated powders, unlike the unprocessed original fine powders.

It was found that the compacts made with the MECHANOFUSed SORBOLAC 400 with 5% magnesium stearate gave some lamination and capping problems. This is indicative of trapped air, and is conventionally associated with high levels of fine cohesive powders in tablet formulations. Compacts made with MECHANOFUSed Extra Fine and 5% magnesium stearate, gave similar lamination and capping problems. With lower levels of magnesium stearate, the problems were reduced.

The SORBOLAC based powders gave stronger tablets than the Extra Fine based powders. As a consequence, the magnesium stearate appeared to provide a significant barrier to forming lactose-lactose contacts in the coated powders, and its use should be minimized. Consequently, a binder was also introduced, to try to improve compact strength. A cellulose based binder was selected due to its known excellent binding properties, and its plastic behaviour, such that it should deform during the contact process.

All MECHANOFUSed powders were then blended w/w with 10% and 30% EMOCELL microcrystalline cellulose with VMD ~50 um as a binder. Once again, tablets were produced under the same compression test. Some lamination/capping problems were evident in some cases, but these were reduced and tablet strength improved in comparison to earlier cases. Povidone was also examined as an alternative binder.

These tests indicated the following:
Reduced particle size appeared to increase resulting tablet strength.
Powder flow appeared sufficient to allow tablet press filling, despite very fine particle size.
Lamination and capping can occur, associated with air trapped by such very fine powders, and formulations require optimisation accordingly.
The level of additives such as magnesium stearate and colloidal silica need to be optimised in each case.
The binder can be added to improve compaction
In some cases, colloidal silica may be a preferred additive as compression may allow it to sink below the surface of the particles, hence reducing its lubricant activity.

Example 10

A model poorly soluble drug, indomethocine was milled in an AVESTIN high pressure homogenizer in water with sodium lauryl sulphate, to a median particle size of about 500 nm. The powder was recovered by spray drying. This powder was then mechanofused in a MECHANO-FUSION AMS-Mini (Hosokawa) with lactose (SORBOLAC 400) with a mass median particle size of about 8 microns in the ratio 10:1 by weight. The sample was premixed for 5 minutes by running the machine at 1000 rpm. The machine speed was then increased to 5000 rpm for 10 minutes.

This powder was then suitable for incorporation into a tabletting blend, optionally with other excipients, or could be employed in a powder formulation for oral delivery.

The powders of the invention, as exemplified in the examples above, may be combined with further materials and compacted and formed into tablets by standard tabletting methods, such as an automated tablet machine, known in the art.

The powders of the invention, as exemplified in the examples above, may be combined with further materials and filled into, e.g. gelatine or HPMC capsules.

The invention claimed is:

1. A powder comprising:
   a plurality of additive coated host particles comprising a plurality of host particles and an additive coating material mechanically fused onto the plurality of host particles by high shear and compressive forces such that the additive coating material is thinly coated to form a layer of on average less than 1 μm on individual host particles of the plurality of host particles and covers at least 50% of a total surface area of the plurality of host particles;
   wherein the additive coating material is at least one of a lubricant and an anti-adherent;
   wherein the plurality of additive coated host particles have at least one of a bulk density and a tap density of at least 25% more than that of an equivalent unprocessed host material with the same size distribution;
   wherein at least 80% by mass of the plurality of additive coated host particles have a geometric diameter of 100 microns or less, and the plurality of additive coated host particles have a mass median diameter of greater than 10 μm and less than 60 μm; and
   wherein the plurality of additive coated host particles define a particle-particle contact with one another and cohere when subjected to a compressing force.

2. The powder as claimed in claim 1, wherein at least one of the plurality of additive coated host particles comprise un-agglomerated micro particles.

3. The powder as claimed in claim 1, wherein the at least one of the anti-adherent and the lubricant is selected from the group consisting of a metal stearate; salts, esters and other derivatives of stearates, palmitates, behenates and other fatty acids having a carbon chain length of C6 to C35, including saturated as well as unsaturated chains, cis and trans isomers; sodium stearyl fumarate; glyceryl behenate; sodium stearyl lactylate; sodium lauryl sulphate; and leucine.

4. The powder as claimed in claim 1 wherein at least one additive coated host particle comprises a host particle covered by a continuous coating of the additive coating material.

5. The powder as claimed in claim 1 wherein the additive coating material is fused to surfaces of the plurality of host particles to provide a discontinuous coating covering at least 70% of the total surface area of the plurality of host particles.

6. The powder as claimed in claim 5 wherein the additive coating material of the plurality of additive coated host particles is on average less than 0.5 μm thick.

7. The powder as claimed in claim 1 comprising a bi or multi-modal size distribution.

8. The powder as claimed in claim 1, wherein the plurality of additive coated host particles are obtained by a mixing process comprising a rotor rotating relative to a vessel at a speed of greater than 2,000 rpm for a predetermined duration.

9. A method of manufacturing a powder, comprising:
   forming a plurality of additive coated host particles by mixing a plurality of host particles with 3% or less of an additive coating material by weight of the plurality of additive coated host particles, the additive coating material composed of at least one of an anti-adherent and a lubricant, wherein mixing the plurality of host particles with the additive coating material includes mechanically fusing the additive coating material onto the plurality of host particles via a high energy mixing process under conditions of high shear and compressive forces sufficient to thinly coat individual host particles of the plurality of host particles with the additive coating material to form a layer of on average less than 1 μm and cover at least 50% of a total surface area of the plurality of host particles;

wherein the plurality of additive coated host particles have a mass median diameter of greater than 10 µm and less than 60 µm;

wherein the plurality of additive coated host particles have at least one of a bulk density and a tap density of at least 25% more than that of an equivalent unprocessed host material with the same size distribution, as measured according to U.S. Pharmacopeia; and wherein the plurality of additive coated host particles cohere together when subject to a compressing force.

10. The method as claimed in claim 9, wherein mechanically fusing the additive coating material onto the plurality of host particles includes mechanically distorting the additive coating material onto the plurality of host particles with sufficient force to locally heat and wrap the additive coating material at least partially around the plurality of host particles and form a coating.

11. The method as claimed in claim 9, wherein the at least one of the anti-adherent and the lubricant of the additive coating material includes leucine.

12. The method as claimed in claim 9, wherein mixing the plurality of host particles with the additive coating material forms a discontinuous coating that covers at least 70% of the total surface area of the plurality of host particles.

13. The method as claimed in claim 9, wherein the at least one of the anti-adherent and the lubricant is selected from the group consisting of a metal stearate; salts, esters and other derivatives of stearates, palmitates, behenates and other fatty acids having a carbon chain length of C6 to C35, including saturated as well as unsaturated chains, cis and trans isomers; sodium stearyl fumarate; glyceryl behenate; sodium stearyl lactylate; and leucine.

14. The method as claimed in claim 9, wherein mixing the plurality of host particles with the additive coating material results in mechanically distorting the plurality of additive coated host particles to provide the plurality of additive coated host particles with a Carr index of less than 0.35 and an angle of repose less than 40 degrees.

15. The powder as claimed in claim 1, wherein the at least one of the lubricant and the anti-adherent of the additive coating material includes leucine and covers at least 50% of a total surface area of the plurality of host particles.

16. The powder as claimed in claim 1, wherein the plurality of additive coated host particles have a Carr index of less than 0.35 and an angle of repose less than 40 degrees.

17. The powder as claimed in claim 1, wherein the plurality of additive coated host particles have a spherical shape.

18. The powder as claimed in claim 1, wherein the additive coating material of the plurality of additive coated host particles is on average less than 0.5 µm thick and the additive coating material constitutes 3% or less by weight of the plurality of additive coated host particles to facilitate coherence of the plurality of additive coated host particles.

19. The method as claimed in claim 9, wherein mixing the plurality of host particles with the additive coating material is performed by rotating a rotor in a vessel at a speed of greater than 2,000 rpm for a duration of 10 minutes to 30 minutes.

20. A compact comprising the powder as claimed in claim 1.

* * * * *